United States Patent [19]

Hogan

[11] Patent Number: 5,061,235
[45] Date of Patent: Oct. 29, 1991

[54] PORTABLE SUPERABSORBANT PERSONNEL STRETCHER AND ERECTABLE ON-DEMAND ISOLATION TENT

[75] Inventor: John D. Hogan, Gloucester, Mass.

[73] Assignee: Beth Israel Hospital Association, Boston, Mass.

[21] Appl. No.: 445,008

[22] Filed: Dec. 4, 1989

Related U.S. Application Data

[63] Continuation-in-part of Ser. No. 142,077, Jan. 11, 1988, Pat. No. 4,885,000, which is a continuation-in-part of Ser. No. 1,648, Jan. 9, 1987, abandoned.

[51] Int. Cl.[5] .......................................... A61G 1/100
[52] U.S. Cl. ....................................... 600/21; 604/358; 5/82 R; 27/28; 294/140
[58] Field of Search .................. 604/356, 358; 600/21, 600/22; 5/82, 89, 413; 294/140; 296/20; 27/23.1, 28; 312/1; 128/870

[56] References Cited

U.S. PATENT DOCUMENTS

| | | |
|---|---|---|
| 3,272,199 | 9/1966 | Matthews . |
| 3,492,987 | 2/1970 | Parker . |
| 3,798,685 | 3/1974 | Hunt et al. ............................. 5/82 |
| 3,986,505 | 10/1976 | Power ..................................... 5/82 |
| 4,224,936 | 9/1980 | Cox . |
| 4,275,719 | 6/1981 | Mayer . |
| 4,335,712 | 6/1982 | Trexler . |
| 4,367,728 | 1/1983 | Mutke . |
| 4,605,029 | 8/1986 | Russell ................................... 5/413 |
| 4,627,426 | 12/1986 | Wegener et al. .................... 604/358 |
| 4,772,281 | 9/1988 | Armstead ............................ 604/358 |
| 4,790,051 | 12/1988 | Knight ................................... 27/28 |
| 4,876,773 | 10/1989 | Wade .................................... 600/21 |
| 4,885,000 | 12/1989 | Hogan ................................... 600/21 |
| 4,922,562 | 5/1990 | Allred et al. ........................ 128/870 |
| 4,939,803 | 7/1990 | Waters .................................... 5/87 |

FOREIGN PATENT DOCUMENTS

| | | | |
|---|---|---|---|
| 1131359 | 6/1962 | Fed. Rep. of Germany .......... | 27/28 |
| 2271805 | 12/1975 | France ..................................... | 5/82 |

Primary Examiner—Stephen C. Pellegrino
Assistant Examiner—Ralph A. Lewis
Attorney, Agent, or Firm—David Prashkee

[57] ABSTRACT

A portable superabsorbent personnel stretcher and exactable on-demand isolation tent article is provided which is easily transportable, durable, and can be prepared in both sterile and non-sterile formats. The combination superabsorbent stretcher and isolation tent provides a fluid-absorbing capacity and capability via fibers able to absorb at least 15 times their own weight in fluid. The invention also provides portable means for erecting the collapsed isolation tent on-demand and portable means for transporting the combined stretcher and isolation tent in both collapsed and erected states.

18 Claims, 7 Drawing Sheets

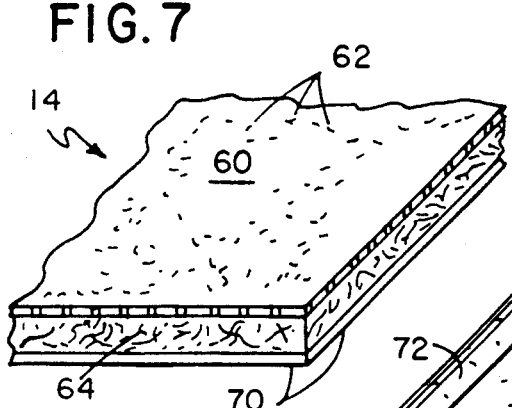
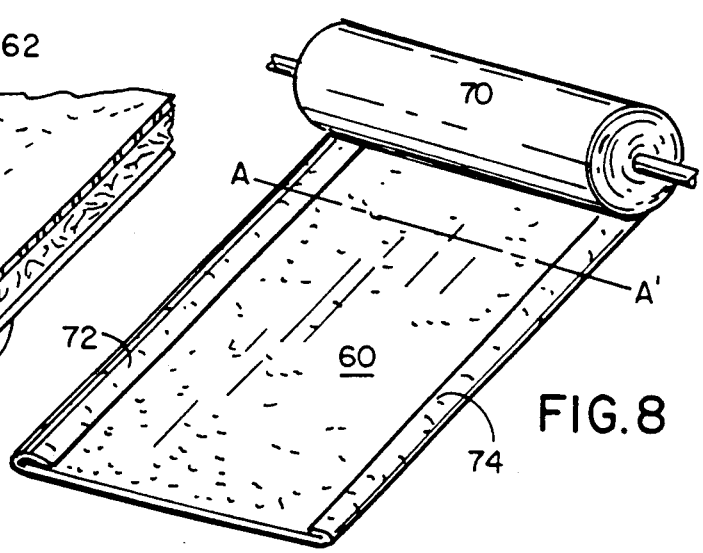
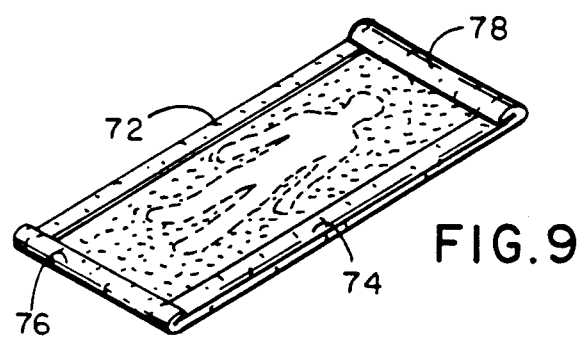
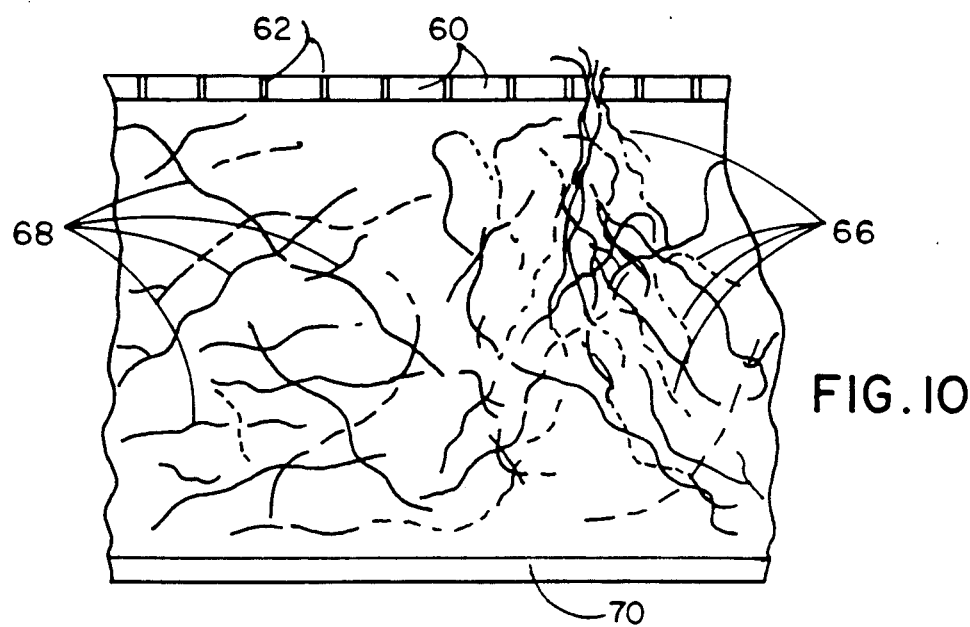

PORTABLE SUPERABSORBANT PERSONNEL STRETCHER AND ERECTABLE ON-DEMAND ISOLATION TENT

CROSS-REFERENCE

The present application is a continuation-in-part of application Ser. No. 142,077 filed Jan. 11, 1988, now U.S. Pat. No. 4,885,000, which was a continuation-in-part of application Ser. No. 001,648 filed Jan. 9, 1987, abandoned.

RESEARCH SUPPORT

The research for the present invention was supported by the Beth Israel Hospital Association.

FIELD OF THE INVENTION

The present invention is concerned generally with improvements in emergency stretchers and litters commonly used by emergency medical personnel and technicians in ambulances, emergency rooms, and trauma centers; and is particularly directed to improvements in portable stretchers which markedly reduce the risk of accidental infection and contamination of medical personnel from potentially hazardous body fluids and liquid waste released by an infected or injured subject both during life and after death.

BACKGROUND OF THE INVENTION

It is commonly recognized that persons who have been traumatically injured or are afflicted by disease or a disorder have physical injuries and/or gross symptoms which are typically accompanied by the release of potentially infectious blood and other body fluids which may harbor bacteria, viruses, or other hazardous and toxic agents. The variety of potentially hazardous body fluids and liquid wastes includes not only infectious blood, lymph fluid, sputum, and the other body fluids comprising or protecting the major tissues and organs internally; but also urine, excrement, fouled water, ambient hazardous chemicals and toxic agents, mud and other soil mixtures, as well as other major parts of the environment in which the individual works or lives. These potentially hazardous fluids may then contaminate, injure, or infect the emergency medical personnel; the physicians, surgeons, nurses, and technicians within the emergency room or trauma center; other patients and persons in the general hospital environment; and, all too often, the pathologists and attendants examining the body tissue or performing the autopsy, especially when a lethal and possibly contagious agent or disease was the true cause of death. The containment of such potentially hazardous body fluids and liquid wastes from or used in conjunction with a diseased or injured person is a "universal precaution" of major importance; and such "universal precautions" are currently under increasing scrutiny and governmental regulation to provide improved protective general procedures in order to avoid and prevent possible infection and contamination of medical and technical personnel.

It has now been well recognized that current procedures for removing potentially hazardous body fluids and liquid wastes released by a living or dead person during medical treatment or via autopsy are often inadequate, inefficient, or actually hazardous. Often, body fluid and liquid waste is absorbed only via the use of bulky sheets or drapes with minimal absorptive capacity; such articles can not usually absorb the quantity of released fluid and then typically drip the fluid and other liquid waste onto the surrounding environment and supporting personnel, particularly when the subject is moved from place to place.

In addition, it is often very desirable to isolate a patient as soon as possible in order to provide two different kinds of protection. These are: protection of the injured and sick from potential exposure to contaminants in the air; and protection of attendants and workers from the contaminated body fluids and wastes released by the sick or injured.

The protection of the sick and injured is often a critical requirement. For example, a burn victim, having lost the use of his protective skin layer, is very vulnerable to incidental infection and should be isolated from potential contaminants present in the ambient environment. Similarly, an AIDS patient is very prone to infection since the HIV virus has meaningfully disabled the victim's immune system and substantially lowered the patient's ability to resist disease. Other instances would include a cancer patient undergoing chemotherapy which concomittantly renders the cancer patient vulnerable to acquiring accidental infections from the environment. All of these persons would fare markedly better if they were isolated from the ambient environment during their medical treatments.

The alternate form of protection provided by isolation is intended for those persons in close contact with the sick or injured patient. In many instances also, when unfortunately the subject has died of his injuries or disease, it is also then desirable to isolate the corpse of the subject. Nevertheless, particularly in autopsy and embalming procedures, the potentially hazardous body fluids and liquid waste is often allowed to drain directly into septic systems. In addition, these procedures typically lead to contamination of the skin, clothing, and person of the attending personnel; and all too often contaminate the equipment, furniture, and the general surrounding environment where the corpse is held. In such instances, isolation is extremely important to protect the physicians during autopsy and the embalming personnel especially when a lethal and possibly contagious disease was the cause of death of the subject.

The severity of the problem is best illustrated and understood by following the normal course of events which typically occur after a call for an ambulance or emergency medical personnel has been initiated to a particular site. A standard part of the equipment that an ambulance and emergency medical personnel bring to the wounded or infected person is a stretcher—destined for aiding and supporting the injured or sick person from the original site where found to an emergency room or trauma center. The typical stretcher is an upholstered or cushioned bed supported on a frame and has wheeled collapsible legs which aid in the moving of the body of the person after placement on the stretcher. All too often the stretcher itself is covered merely with a thin fibrous sheets and/or blankets upon which the injured or infected person is placed. Typically, the medical attendants roll up the side of the sheet and blanket to prevent the body fluids (including blood and human waste) from dripping onto their person or from splattering the general environment surrounding the place where the patient has been found.

As an aid, absorbent padding is in wide spread use, typically as wedges, bolts, sponges, or other shapes of cloth placed along the perimeter or edges of the stretcher to help prevent the dripping of the potentially hazardous fluids and to minimize the contamination of the local geographical area. Many of these aids incorporate fluid-absorbing materials, often in powdered or particulate form. Unfortunately, such fluid absorbing aids have major deficiencies: frequently they absorb only limited amounts of fluids, typically only a maximum of 10 fold its weight in water or other fluids. Many of these absorbents are not readily fixed in place within a fibrous weave or cloth; consequently, when wet, these materials tend to clump and displace in volume and position. More importantly, even the superabsorbent "gel blocks" become far less absorbent when the top of the material becomes saturated causing the product to ooze and dispel fluid when saturated, particularly under pressure circumstances. In addition, these gel products typically wick fluid across their top surfaces; and thus may actually increase the risk of potential contamination of the entire fluid absorbing material and the medical personnel holding them in position.

Another major flaw in the stretcher apparatus presently used by emergency medical personnel is the general inability to isolate the body of the injured or diseased patient at least until reaching the hospital emergency room or trauma center. In many emergency procedures and instances, it is most desirable to isolate the body of the injured or diseased person as soon as possible. Such isolation is critical, as noted previously, not only to protect the injured or diseased person from contamination by the ambient environment; but also to prevent the potential contamination, infection, or transmission of highly infectious diseases, fluids, or other hazardous and toxic agents to the attending medical personnel. Note that the blood and other fluid typically dripping from the bedding is due in part to the weight of the patient. When the patient is physically picked up for transfer, the weight of the patient causes the sheets to form a hammock and thus forms a valley into which the fluids run. Also the weight of the patient actually squeezes fluid out of the wetted bedding. Unfortunately, present practices do not provide any effective, portable isolation tent apparatus by which to isolate the injured or perhaps even dying person while lying on the stretcher during initial examination at the site of injury or discovery, or during transport to the hospital emergency room or trauma center.

The critical event thus typically occurring upon entering the receiving room of the hospital or trauma center is a physical transfer by medical personnel of the patient from the portable stretcher bed to a fixed examination table. In common occurrence, the injured or diseased patient becomes surrounded by additional medical personnel now including specialized surgeons and physicians in an effort to determine the status and speed of treatment required for the particular individual. All too often, the bedding (and released fluids) on the portable stretcher is merely rolled up and discarded as trash; or even in some instances laundered and used again for the next medical emergency to come. With the increasing dangers caused by potentially infectious blood and other body fluids which may contain the human immune deficiency virus causing AIDS, the hepatitis B virus, or the tuberculosis bacteria, new procedures for disposing of the bedding are only now being contemplated.

Once the injured or diseased person has been removed and placed upon a hospital examination table, he then may be isolated as required or necessary using known isolation tents or other isolation apparatus. The bedding, however, upon which the patient lies then accompanies him during the subsequent transfers to other tables, gurneys, and other stretchers or litters to isolation wards, surgical operating rooms, post-surgery recovery rooms, etc.; this bedding remains a serious risk to medical personnel because of the continuing release of potentially infective blood and other body fluids during the emergency treatment process.

In addition, following an emergency treatment procedure where a certain amount of urgency and disciplined chaos are frequently present, a variety of sharp-edged articles such as scalpels, syringe needles, and the like may accidently become lost or intermingled in the sheets of the bedding. After the patient has been physically moved onto a different stretcher (as in the emergency room), someone else comes to clean up the debris left in the aftermath. This person, while in the act of gathering up the sheets and bedding, frequently is punctured by a hidden sharp-edged instrument inadvertently left in the sheets or bedding; and can become accidently infected by the infectious blood, fluids, and other wastes on the instrument and in the surrounding bedding.

The sequence of events taken to its undesirable but logical conclusion ends in the autopsy room for the pathological workup and report. Unfortunately, there is a major risk of infection for autopsy personnel which can occur both during the performance of the autopsy and during the subsequent cleaning-up process. Blood spills, pieces of tissue, and other fluid and liquid matter associated or obtained via the autopsy can soil personnel clothing, surrounding equipment, tables, and even the floors within the autopsy room—hereby creating major risks of contamination and infection to involved personnel. It has recently become apparent that the equipment, autopsy procedures, and clean-up methods that should be utilized during and after the performance of an autopsy should minimize the risk of potential infection or contamination from the corpse being examined. In this manner, isolation apparatus surrounding the corpse have been employed to contain the body matter, prevent the spread or exposure of microorganisms from becoming airborne generally, and to provide a convenient and safe method by which to remove those necessary parts of the corpse both during and after the autopsy. Equally important, those persons in the funeral industry which subsequently receive the body for embalming and burial or other disposition become at risk also because they become exposed to the body fluids and liquid wastes released by the corpse as a concommitant part of handling the corpse for funeral purposes.

It is abundantly clear, therefore, that the risk of potential contamination, infection, and other direct injury remains a real and relatively constant threat and danger to medical personnel and other persons coming into contact with either the living injured or diseased person, or the subsequent corpse. It is now also recognizable that the broad variety of known innovations, customary protective measures, and conventional tangible means for protecting attending medical personnel are in the main limited to specific use circumstances of relatively short duration and effectiveness; and moreover, are not themselves useful or convenient for prolonged use or effect over the common sequence of events occurring from the moment the ambulance and emergency medical personnel arrive at the site of finding the injured or diseased person, through the intervening events up to and including the performance of an autopsy procedure, and the subsequent embalming and disposition of the corpse by funeral personnel.

A summary review of the presently available protective devices, articles, and isolation apparatus reveals the inherent limitation and general unsuitability of these conventionally known devices and protections to follow the individual person from the site of injury or disease; through the sequence of treatments by ambulatory medical personnel and hospital physicians and surgeons; and then through the unfortunately ultimate conclusiory events of autopsy and funeral disposition. For example, a variety of fluid-absorbent fabrics and fibers are known which are useful both as wound dressings and as protective garments in the operating room. These include: British Patent No. 2,175,210; French Patent No. 2,565,110; and U.S. Pat. Nos. 4,748,065; 4,637,820; and 3,521,624. Similarly, a variety of different isolation tents and apparatus is illustrated by French Patent No. 1,506,930; and U.S. Pat. Nos. 3,492,987; 3,364,928; 4,224,936; 4,275,719; 4,335,712; 4,367,728; 4,598,487; and 4,675,923 respectively.

Despite these many innovations and improvements in protective and isolation articles and apparatus, there remains a demonstratable and long standing need for a portable personnel stretcher apparatus which has the capability of isolating the injured or diseased patient at the time of discovery; and maintaining the injured or diseased person in a protected and isolated state such that the attending medical personnel and the surrounding environment remain substantially free from and protected from the effects of potentially hazardous body fluids and liquid wastes released by the injured, diseased, or deceased person being attended. Insofar as is presently known, there is no single article or apparatus which is able to be utilized at the first instance of finding, discovering, or treating an injured or diseased person; and which is then able to accompany the person being treated through all sequential and subsequent events up to and including autopsy and funeral disposition.

SUMMARY OF THE INVENTION

The present invention is a combination portable, superabsorbent personnel stretcher and erectable, on-demand isolation tent article. This combined stretcher and isolation tent article comprises only five essential parts. These are: at least one planar support sheet having a determinable configuration and dimensions; at least one superabsorbent, fibrous layer disposed upon the support sheet, this superabsorbent layer comprising fluid-absorbing fibers able to absorb at least 15 times their own weigh of fluid; a collapsed isolation tent joined to the support sheet, this collapsed isolation tent being erectable on-demand to envelope and isolate the air space adjacent and surrounding the superabsorbent fibrous layer; portable means for erecting the collapsed isolation tent on-demand; and portable means for transporting the support sheet, the superabsorbent, fibrous layer, and the isolation tent in collapsed and erected states as a single article.

This portable stretcher and erectable isolation tent combined article is intended to replace the presently used bedding, absorbent cloths, and other fluid containing measures presently employed by emergency medical personnel upon their ambulatory stretchers and litters; and provides an isolation capability effective on-demand to encompass and seal-off a person, living or dead, placed upon the stretcher and to isolate the air space adjacent to and surrounding the body of the person indefinately from the moment of discovery through all medical and other treatments including autopsy and final body disposition to funeral directors for embalming. The combination stretcher and erectable isolation tent article can be prepared in presterilized form if desired; can be disposed at will completely and effectively at any stage during the treatment or body disposition sequence of events; and will at all times act effectively to absorb and retain such body fluids and liquid wastes released by the person during life and after death.

BRIEF DESCRIPTION OF THE FIGURES

The present invention may be more easily and completely understood when taken in conjunction with the accompanying drawing, in which:

FIG. 7 is a perspective view of one preferred embodiment for the superabsorbent, fibrous layer comprising part of the present invention;

FIG. 8 is a perspective view of the preferred embodiment of the superabsorbent, fibrous layer supplied in rolled-up format;

FIG. 9 is a perspective view of the preferred embodiment comprising the superabsorbent, fibrous layer with folded-over ends; and FIG. 10 is a diagrammatic cross-section illustration of a portion of the non-woven matrix comprising the preferred embodiment of the superabsorbent, fibrous layer of the present invention.

DETAILED DESCRIPTION OF THE PREFERRED EMBODIMENT

Figure 1:
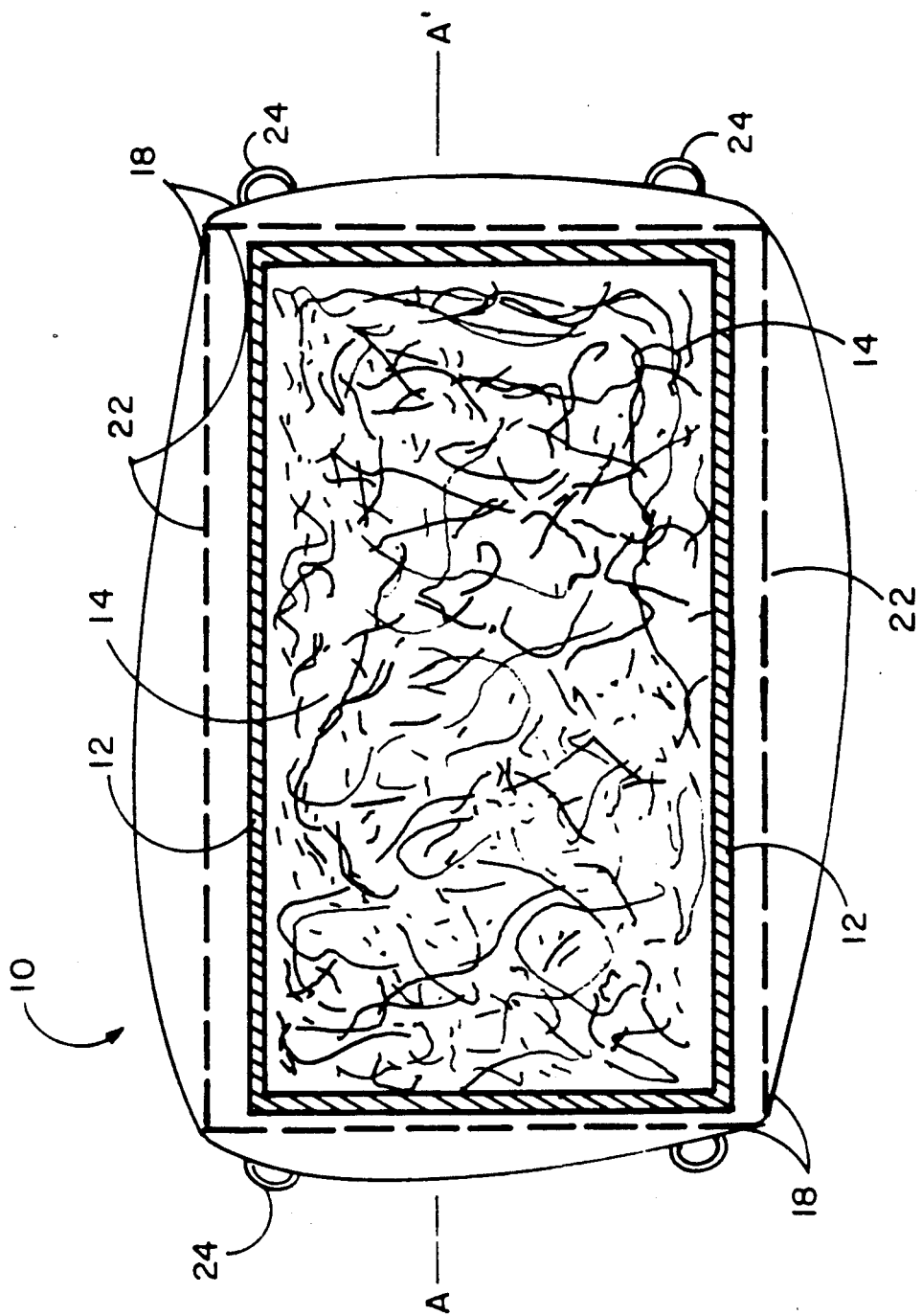
FIG. 1 is an overhead view of one preferred embodiment of the present invention comprising the superabsorbent personnel stretcher and isolation tent in a collapsed state.

The present invention is a combination superabsorbent stretcher and erectable, on-demand isolation tent article prepared as a single, unitary construction. The combination stretcher and erectable isolation tent article is durable, portable, and intended as a complete replacement and substitute for the ambulatory litters, body blankets, emergency personnel carriers, and the like now commonly employed by emergency medical personnel, ambulances, firemen, and even hospital emergency room and trauma center attendants. The present portable stretcher and isolation tent combination can be carried and transported as a discrete article in folded or unfolded form and prepared in either presterilized or non-sterilized form.

The portable stretcher and isolation tent article can be easily hand carried, or transported by ambulance or other emergency vehicle to the exact location where the injured or diseased person is initially to be found. At that time, the person, either living or deceased, is placed upon the portable stretcher; and can be immediately isolated from the emergency medical personnel and the ambient environment by immediately erecting the isolation tent feature of the present invention. Upon arrival at the hospital emergency room or trauma center, the injured or diseased person, whether or not isolated, can remain reclined upon the surface of the superabsorbent stretcher for the entirety of the initial medical examination and treatment performed by hospital physicians, surgeons, and technicians. If immediate surgery or other medical tests are required, the injured or diseased person can be transported while still reclining upon the superabsorbent stretcher to the appropriate surgical operation room, x-ray room, or other treatment rooms wherever their location within the hospital or institution. Alternatively, should the person lying on the superabsorbent stretcher fail to respond to emergency medical treatment or be pronounced as dead upon arrival, the corpse would remain lying upon the superabsorbent stretcher which is then used as a litter to transport the body into the morgue, autopsy room, or other designated place.

It is intended and expected that a complete autopsy, if necessary or required, can be performed while the corpse remains positioned upon the same superabsorbent stretcher which originally transported the body to the hospital emergency room or trauma center. Moreover, it is also intended and expected that upon completion of the autopsy and release of the corpse to the immediate family, that the person (in isolated or non-isolated condition) would remain upon the same superabsorbent stretcher which then could be used to transport the corpse to the funeral parlor or other final resting place for disposition. In short, the portable superabsorbent stretcher and erectable on-demand article is purposefully designed and expected to carry and follow the injured/diseased person or corpse from the original site of discovery, through initial transport to the hospital emergency room or trauma center, through emergency medical treatment or other immediate medical attention, and even through the eventual and unfortunate consequence of autopsy and final transport to the funeral directors for final disposition of the body.

In order to provide such a multifaceted service, utility, and following through the entire series of medical events which are possible following serious injury or infection, the present invention requires only five component parts. These are: at least one planar support sheet having determinable dimensions and configuration and preferably formed of weight-bearing material; at least one superabsorbent, fibrous layer disposed upon and preferably attached to the planar support sheet, this superabsorbent layer comprising fluid-absorbing fibers able to absorb at least 15 times their own weight of fluid and preferably able to absorb as much as 50 times their own weight in fluid; a collapsed isolation tent joined and sealed fluid-tight to the planar support sheet, this collapsed isolation tent being erectable on-demand to envelope a subject resting on the superabsorbent fibrous layer and to isolate the air space adjacent to and surrounding the subject and the superabsorbent, fibrous layer; portable means for erecting the collapsed isolation tent on-demand at any geographical location or site; and portable means for transporting the unitary article comprising the planar support sheet, the superabsorbent fibrous layer, and the isolation tent whether in collapsed or erected state.

From the foregoing description of intended application and use and by the disclosed description and definition of its component parts, it is clear that the present invention provides multiple, major, and unique benefits and advantages which were not previously available by conventionally known litters or isolation apparatus. These include:

1. The present invention is easily portable, durable, and able to accommodate itself effectively in a wide variety of different use locations, settings, and circumstances.

2. The present invention is a superabsorbent article comprising a fibrous layer able to absorb at least 15 times and preferably up to 50 times its own weight of fluid. In a preferred embodiment, the superabsorbent fibrous layer is a multi-laminate construction which can be detached and replaced at will by another similarly sized fibrous layer cut from a roll or bolt as needed. In this manner, a superabsorbent fibrous layer previously employed on one occasion may—at one's option and choice—be easily substituted and replaced by another similarly configured and dimensioned one without discarding or disposing of the other component parts of the combined article comprising the present invention.

3. The isolation tent is erectable and collapsable on-demand at any time and at any location from the site of initial discovery or finding of the injured/diseased person or body up to and including the final transportation of the corpse to the funeral directors for final disposition. The isolation tent feature and component may be erected and collapsed and erected again once or many times as the need or situation requires. For both convenience and ease of transport, in the preferred embodiments of the present invention, the isolation tent is held and contained within a closed pouch or elongated bag container having a sealable closure along its length. The pouch or elongated bag container holds the isolation tent in folded or collapsed form; and also serves to keep the tent surface clean until required to be erected This also provides the capability to sterilize the isolation tent and enclosing pouch in advance of use thereby providing a sterilized isolation tent which can be erected on-demand for added protection of patient or medical personnel if and when required.

4. The isolation tent in its multifaced construction also provides for a variety of access routes and conduits through the fabric of the isolation tent such that the emergency medical personnel can both touch and reach the person enveloped and isolated within the tent. The access routes allow direct and intimate therapeutic or other medical treatments through the tent fabric directly to the person within.

5. The material comprising the isolation tent can be chosen to meet frequently encountered medical situations. In one embodiment, the isolation tent would be formed of clear or radiologically transparent materials. A variety of known polymers and an avoidance of metals would provide this capability. Patients could then be x-rayed or otherwise subjected to prechosen energy wavelength analysis while enveloped within the erected isolation tent. This is important in instances of neck or back injury where the patient is stabilized at the accident scene; and where the patient would be examined by portable x-ray machine prior to removing them to the emergency room.

In another embodiment, the isolation tent would be formed of or be coated with known heat reflecting materials such as aluminum. Such materials and coating would reflect the patient's body heat back into the interior of the erected isolation tent and help prevent hypothermia. In addition, extra heat purposely introduced through the fabric of the erected isolation tent by external heating sources would be retained by radiation from the heat reflecting materials of the tent itself.

6. The election to erect the isolation tent can be made under many different conditions for diverse reasons and uses. The fully erected stretcher and isolation tent creates a portable "coccoon" which can be variously used as: a temporary isolation bed or intensive care unit bed in remote areas or in instances of natural disasters, epidemics, or tragic accidents; a military medical bed in the field or aboard ship which would keep patients protected from the environment as well as from infecting each other; a temporary shelter to protect the injured such as an injured skier from climatic conditions including snowstorms and cold; and as a regularly used hospital bed for persons such as AIDS patients to avoid contamination of mattresses and other permanent hospital equipment and fixtures. Many other use circumstances are envisioned in addition to these.

7. The entirety of the combination superabsorbent stretcher and erectable on-demand isolation tent article can be disposed at will at any time after a single use or after multiple use occasions. The article—then containing and holding all fluids and other liquid waste released by the body or otherwise absorbed by accidental or inadvertent fluid contact—are retained by the superabsorbent fibrous layer. Such retained fluids do not drip, flow, or otherwise release fluid over the volume or perimeter of the stretcher itself. The used stretcher, now containing substantial quantities of fluid and other liquid waste may nevertheless be folded or rolled and discarded or destroyed completely as a single unitary article without any danger of accidental contamination or spillage from the absorbed contents.

In preferred use circumstances, the original packaging for the combined stretcher and erectable isolation tent article will also serve as a disposal bag. The discarded stretcher and isolation tent can be refolded and placed into the packaging whenever desired; the packaging is then preferably resealed prior to actual disposal of the used article. This would keep all retained fluids and all infectious materials and agents generated in caring for the patient within the folded article at all times.

Preferred embodiments of the invention are illustrated via FIGS. 1-6 inclusive. FIG. 1 provides an overhead view of the combination superabsorbent stretcher and erectable isolation tent article 10 which reveals a planar support sheet 12 which preferably is formed of weight-bearing material and is configured as a rectangular sheet of variable thickness. This sheet may be woven or non-woven, formed of natural or synthetic composition, and may be either translucent or not as desired or required by the intended use. In its intended function for the transport of humans or other similarly sized subjects, it is envisioned and expected that the planar support sheet would typically be approximately 7 feet long, 2½ to 3 feet wide, and vary from ¼ inch to several inches in thickness. It is also very desirable that the tensile strength of the planar sheet be at a maximum rather than at a minimum level; and thus be a weight-bearing sheet able to accommodate persons weighing in excess of 300 pounds in the preferred embodiments.

Disposed upon the planar, support sheet 12 is at least one superabsorbent fibrous layer 14. This superabsorbent layer 14 comprises fluid-absorbing fibers able to absorb at least 15 times their own weight in fluid. The spatial configuration and dimensions of the superabsorbent fibrous layer 14 should conform closely if not exactly to the dimensions and configuration of the planar support sheet 12 upon which the superabsorbent layer rests. Within the embodiment of FIG. 1, the superabsorbent fibrous layer is a preferred multi-part laminate construction which will be described in detail subsequently herein. At a minimum, the superabsorbent fibrous layer 14 is a single layer of material which is disposed upon and therefore merely rests on the upper surface 8 of the planar support sheet 12. In the preferred alternative, however, the superabsorbent fibrous layer 14 is secured, in a permanent or detachable manner to the surface 8 of the planar support sheet 12. The permanent or detachable means of securing the fibrous layer 14 are conventionally known and include velcro strips, snaps, buttons, hooks, and any other means of securing commonly known.

Figure 2:
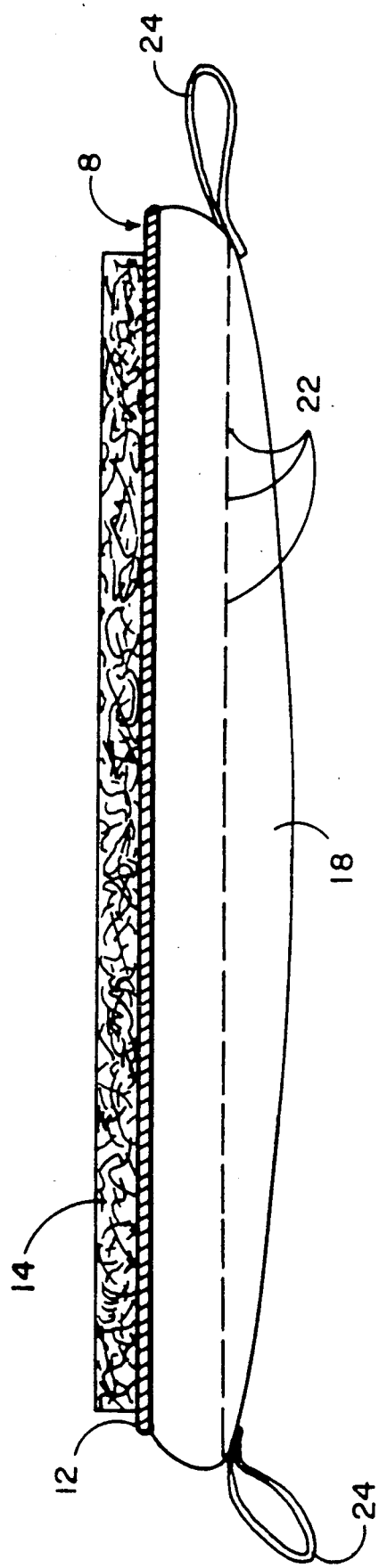
FIG. 2 is a side view of a preferred embodiment illustrated within FIG. 1.
Figure 3:
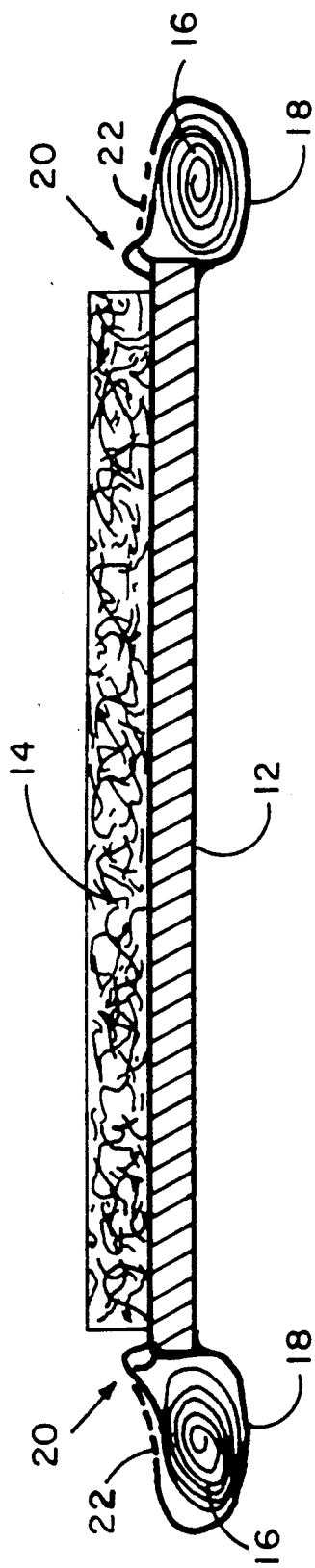
FIG. 3 is a cross-sectional view of the preferred embodiment illustrated within FIG. 1 along the axis AA'.

Surrounding the planar support sheet 12 and the superabsorbent fibrous layer 14 is a collapsed isolation tent 16 which is joined and desirably sealed fluid-tight to the planar weight-bearing sheet 12, preferably along its perimeter or edges. This is best illustrated by the cross-sectional view of the preferred embodiment of FIG. 1 along the axis AA' as illustrated by FIG. 3. As seen therein, the isolation tent 16 is collapsed and folded into a rolled form; and is housed and contained within an elongated pouch 18 whose length is substantially coextensive with the size and dimensions of the isolation tent itself. Nevertheless, it is seen within FIG. 3, that one edge 20 of the isolation tent 16 extends through the holding pouch 18 and is joined directly to the perimeter of the planar support sheet 12 in the desirable fluid-tight, sealed fashion. An elongated closure 22 serves as the point of egress and entry for the edge 20 and the remainder of the isolation tent 16 in the collapsed state. The elongated closure 22 may be of any design and construction; be a single seal or reuseable seal; and vary in size and length according to the needs or desires of its intended user. While in the collapsed or folded state, the isolation tent 16 is desirably held and contained within the elongated pouch 18 as shown in FIGS. 2 and 3 respectively. In addition, as appears in FIGS. 1 and 3, the portable means for transporting the unitary integrated article is provided by a plurality of hand loops 24 which are also preferably attached to the planar support sheet 12. These hand loops are intended to be seized by two or more persons who would then hand-carry a subject resting upon the superabsorbent fiber layer from the original point of discovery to the ambulance or other vehicle for transport to the hospital emergency room or trauma center for further medical attention.

It is clear that the holding pouch 18 is a desirable but not compulsory feature of the present invention. There is no requirement that the isolation tent in its collapsed state be held or carried within any other container or be supported in any manner. To the contrary, it is only essential that the isolation tent be attached to the planar support sheet 12 in a manner such that when the isolation tent is erected, a complete envelope and compartmentalization occurs of the air space surrounding and adjacent to the subject and the superabsorbent fibrous layer itself. In addition, the isolation tent may be composed and formed of any durable material without regard to its chemical composition, weight, or other characteristics. Accordingly, the walls of the isolation tent can be formed of or coated with a heat-reflecting material such as aluminum for improved radiant heating and temperature control within the interior of the erected isolation tent. It is most preferred, however, that the fabric of the isolation tent be translucent or radiologically transparent such that the subject enveloped and isolated may be seen and/or x-rayed directly by the attending medical personnel through the tent; and that the fabric comprising the isolation tent be preferably of durable matter such that it can be sterilized by heat or gas if and when desired.

The preferred embodiment illustrated within FIGS. 1-3, may be itself totally encased within an external container or other packaging (not shown); and be completely sterilized in advance of actual use. The external packaging may subsequently be employed as a disposal bag in preferred embodiments. The unitary article illustrated within these figures may also be prepared as a flat, extended unit; or folded as a bolt of cloth; or rolled into substantially circular or oval form. The folding or rolling of the unitary article provides easier transportation and comfortable portability for the emergency medical personnel. Such folding also provides a minimum of spatial volume for storage purposes until time of actual use.

In addition, the preferred article illustrated by FIGS. 1-3 may be employed with presently existing equipment and support apparatus if desired or required. Accordingly, a preassembled, rectangular stretcher frame may be utilized for further support and easier transport of the invention after a person has been placed on the surface. In addition, in cases of neck or back injury, it is most desirable to place the entire unitary article on a rigid board, plank, or ambulatory table surface to maintain the patient in an immobile, unbent position. Similarly, collapsable, wheeled ambulatory litters now conventionally employed by emergency medical personnel may also be utilized as additional support and transportation needs after a subject has been placed on the superabsorbent fibrous layer of the present invention for additional ease and comfort of the patient. All of these added support devices, immobilization apparatus, and complimenting conveniences are conventionally known and do not in any manner comprise part of the present invention itself.

Figure 4:
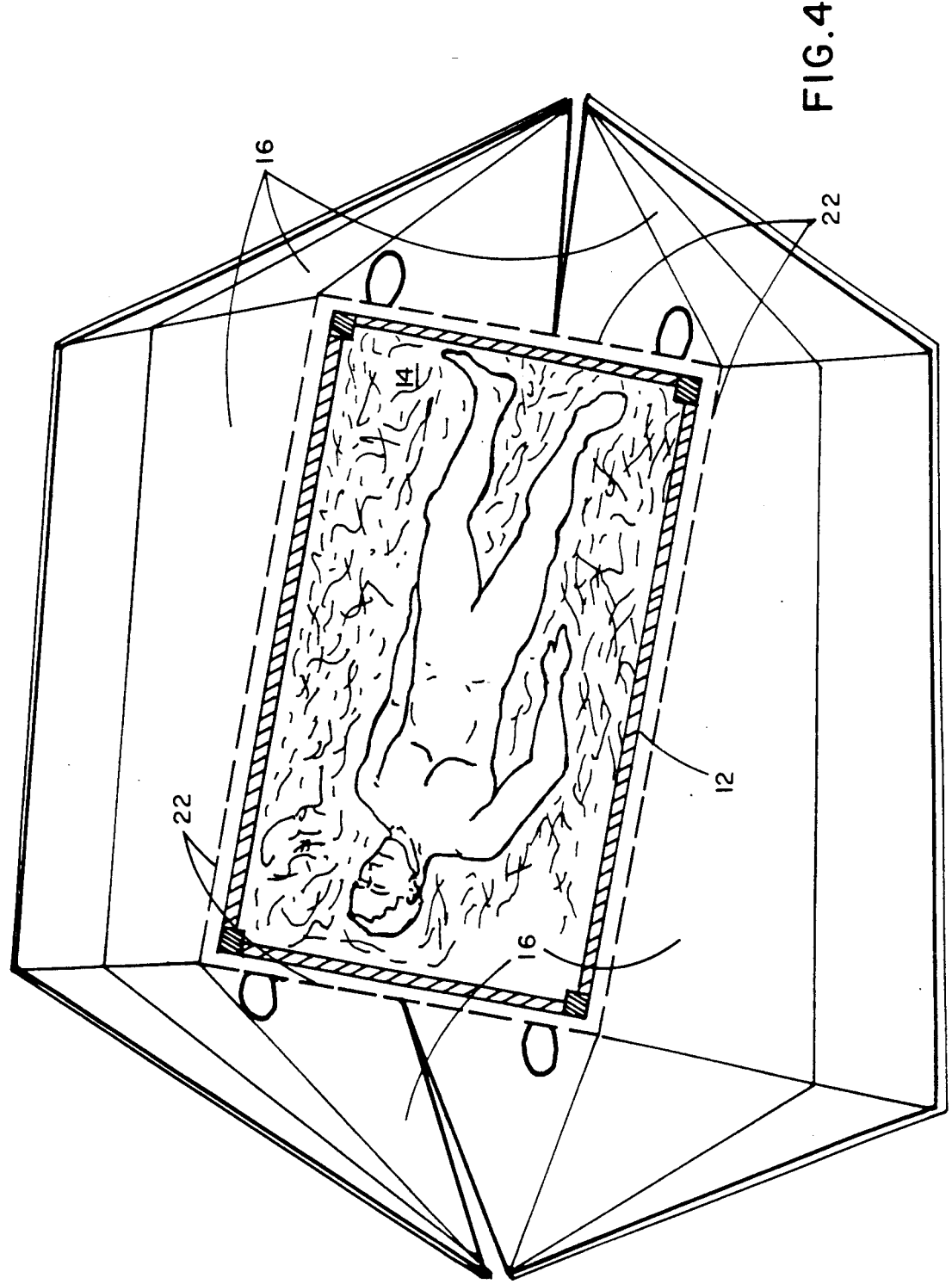
FIG. 4 is an elevated view of the preferred embodiment illustrated within FIG. 1 during which the isolation tent has been extended into a partially erected state.
Figure 5:
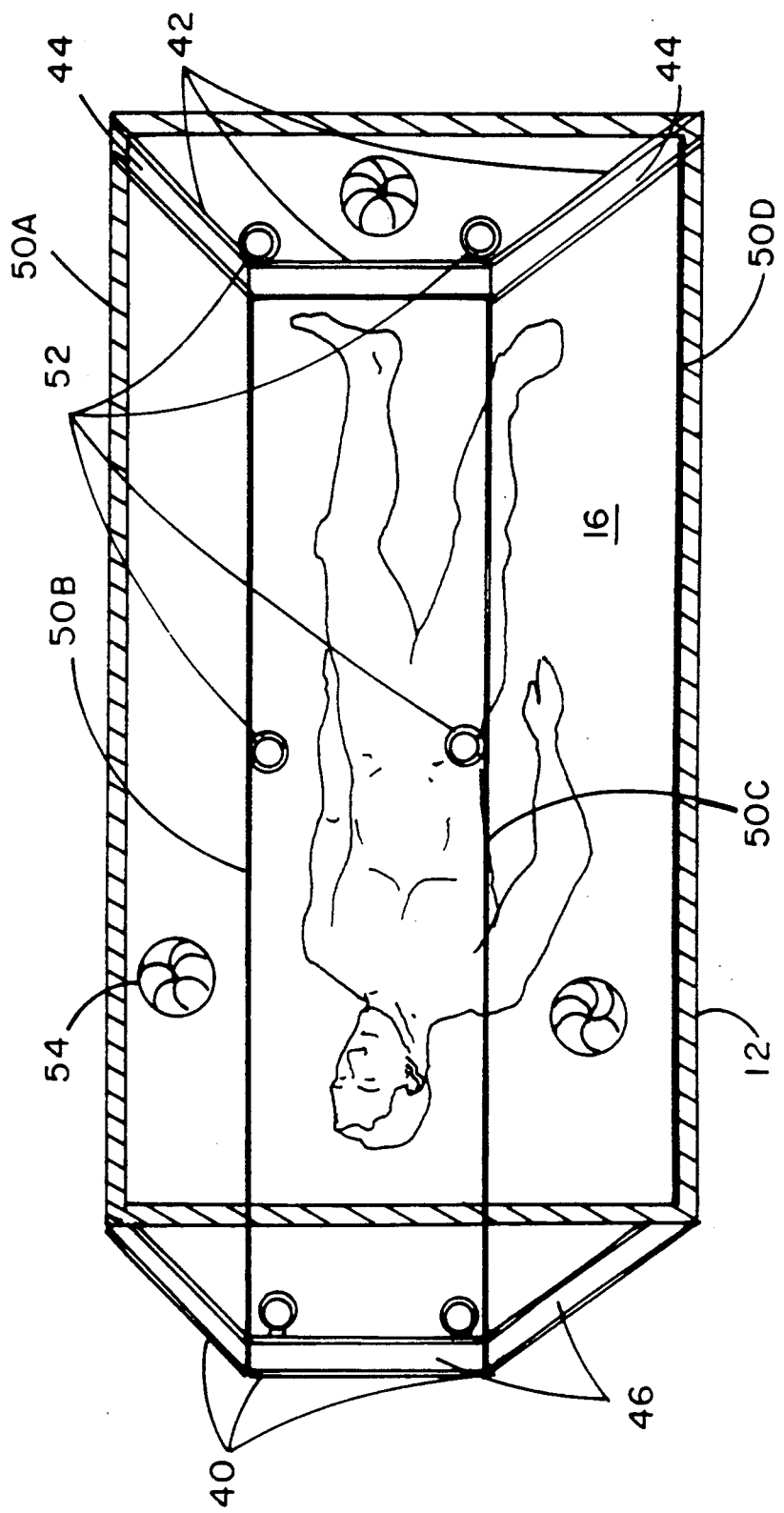
FIG. 5 is an overhead view of the preferred embodiment illustrated within FIG. 1 after complete erection of the isolation tent to envelop and isolate a subject.
Figure 6:
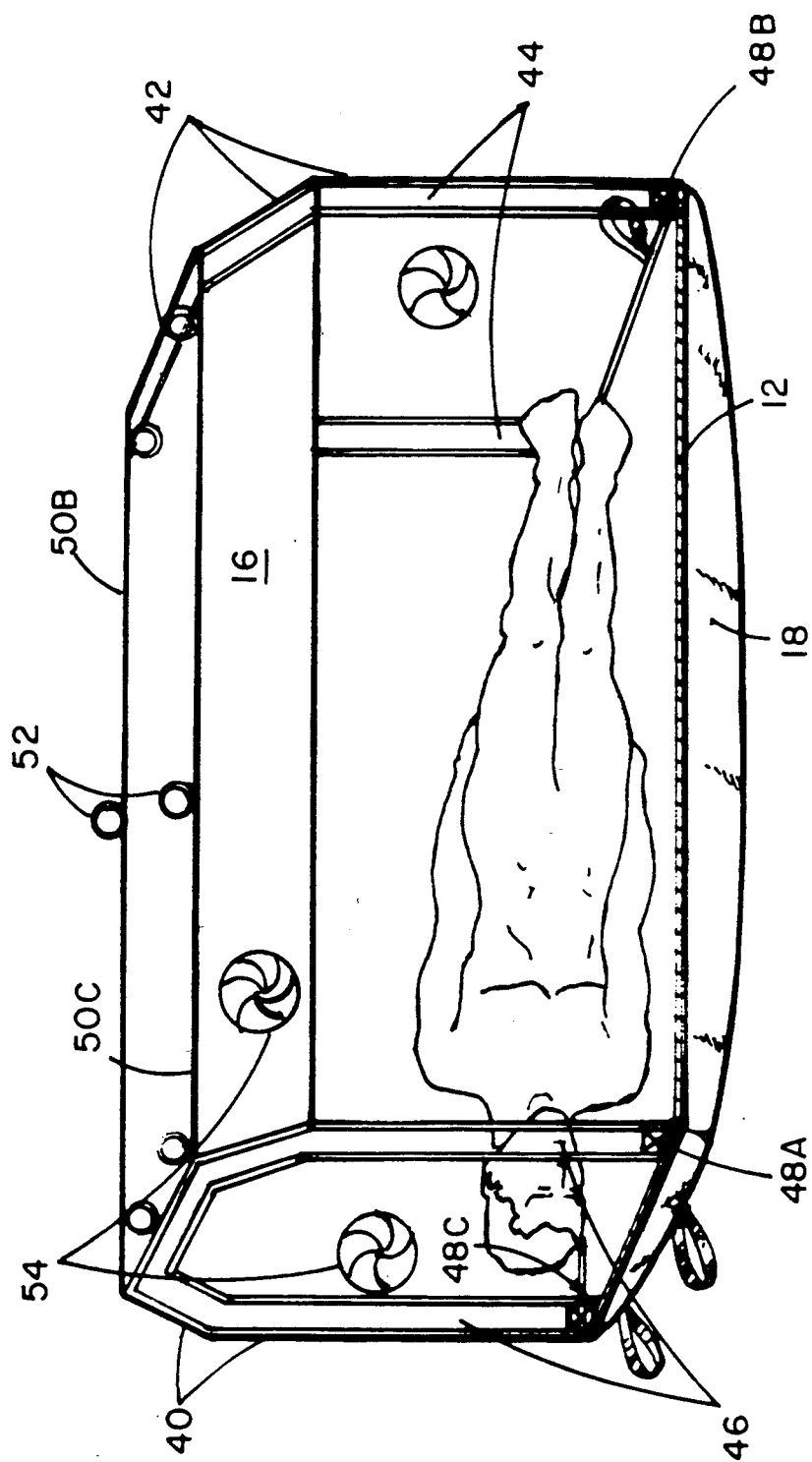
FIG. 6 is a side view of the fully erected isolation tent and superabsorbent personnel stretcher illustrated within FIG. 5.

The on-demand conversion of the collapsed isolation state into a fully erected form is illustrated by FIGS. 4-6 respectively. As seen within FIG. 4, a human subject (living or deceased) has been placed upon the superabsorbent fibrous layer 14. The emergency medical personnel at the scene have made a decision that it is desirable or necessary to immediately isolate the subject now resting on the portable stretcher 10. The closure 22 has been broken or opened; and the isolation tent 16 withdrawn from its holding pouch 18. As seen, the isolation tent 16 has been unfolded and partially extended to reveal the full volume of the isolation tent 16 in a partially assembled state. As the isolation tent 16 is completely unfolded and is fully erected on-site, the other essential components and some optional features of the present invention become visible. These are illustrated by the overhead view of the fully erected isolation tent provided by FIG. 5; and by the sideview of the fully erected isolation tent provided by FIG. 6.

As seen therein, the isolation tent 16 has been constructed and designed in its preferred form to include perimeter sleeves 40 and 42 into which a plurality of interlocked slats or battens 44 and 46 have been inserted. The individual slats 44, 46 are rectangular shaped interlocking constructs of rigid material which have been joined at their edges to provide a portable frame and support for the isolation tent. Each end of the hinged slats 44, 46 is preferably fitted into a bracket holding fixture 48a–48d which has been desirably fastened onto each corner of the upper surface 8 of the planar sheet 12 as seen in FIG. 4. In addition, an optional series of linear stiffening ribs 50a–50d have been previously attached to the longitudinal seams of the isolation tent during its manufacture; and these stiffening ribs have remained within the folds of the isolation tent while in a collapsed state held within the pouch 18. When present, these linear stiffening ribs 50a–50d extend and support the rigidity of the hinged slats 44, 46; and in combination with these slats act to maintain and support the isolation tent in an erected state. It will be recognized that the hinged slats 44, 46, the corner support brackets 48, and the linear stiffening ribs 50 in combination function within the preferred embodiment of FIG. 1 as the portable means for erecting the collapsed isolation tent on-demand; and also serve as the portable means for maintaining the isolation tent in an erected state indefinitely.

It will be appreciated, however, that a wide variety of different portable means for erecting a collapsed isolation tent are conventionally known and available at the present time. Clearly, air insufflation is another viable means for erecting the isolation tent. Air channels would be provided along the edges and seams of the tent fabric; a $CO_2$ cartridge or portable air pump would introduce air into the channels thereby stiffening and holding up the tent in an erect manner. Accordingly, these methods and all alternative or other means which are portable; are able to erect the isolation tent from a collapsed state; and are able to maintain the isolation tent in an erected state for an indefinite period of time are deemed suitable for use within the present invention. Any and all of these conventionally known means are therefore deemed to be within the scope of the present invention.

A number of other desirable, but optional, features of the isolation tent erectable on demand are also illustrated within FIGS. 5 and 6. A series of support rings 52 are preferably attached to the top of the isolation tent fabric and are intended to serve as additional support means for maintaining the isolation tent in an erected state. These support rings 52 are intended to be attached to hooks, levers, rods, bars, belts, loops, supporting frames, and any other device or construction which will help support the weight and volume of the isolation tent itself. Such adjunct means of added erection and support are conventionally known. It is intended and expected that such adjunct hooks, belts, and levers will be found within the interior of an ambulance or other transport vehicle; within examination rooms in hospitals and trauma centers; in surgical operating rooms; in autopsy rooms; and in any other compartment, room, housing, or area where an adjunctive supporting frame or lever can be permanently affixed. A wide and divergent variety of such adjunctive supporting frames and external supports are conventionally known in the art.

In addition, it is most desirable that the isolation tent 16 in its erected state provide at least one sealable porthole or pocket 54 to access the interior of the erected isolation tent and for direct handling of the person enveloped and contained within the erected isolation tent. Such sealable portholes or pockets commonly exist and are conventionally known in a variety of forms, designs, and constructions. As illustrated within FIGS. 5 and 6, the sealable portholes 54 are spaced across the entire fabric and volume of the erected isolation tent 16; and can be selectively positioned anywhere on the fabric of the tent during its construction for the convenience of the attendants. Moreover, although not illustrated, such portholes or pockets may also be sealable with a flap and communicate with the interior of the tent to allow insertion of instruments or other articles into the interior of the isolation tent. The porthole constructions may include sealable flaps able to be opened and closed by a velcro seal; or comprise other means of closure and sealing which will nevertheless provide immediate access through the fabric of the isolation tent to the person contained within without risk of contamination or exposure to the ambient environment or the attending medical personnel.

There are a variety of other features conventionally known which are also desirably, but optionally, present within the invention. These optional features include: conventionally known atomizers disposed along the top or the sides of the isolation tent and in communication through a sealable porthole or pocket with the interior of the tent. Such atomizers may hold a variety of decontaminating sprays which can be activated after the isolation tent has been erected to decontaminate airborne ambient particles or gases inside the erected isolation tent if and when necessary. In addition, such sealable pockets and portholes will be available for such intravenous fluid conduits containing blood, saline, or other liquids which may be packaged in bottle form outside the isolation tent; and whose contents are then passed through the fabric of the erected isolation tent into the person enveloped within. Such optional features, conveniences, and aides are conventionally known; and are described briefly herein for their long-recognized utility and beneficial effect merely as an adjunct to the essential components comprising the present invention.

Details regarding the preferred multi-laminate embodiment of the superabsorbent fibrous layer are illustrated by FIGS. 7–10 respectively. FIG. 7 shows a perspective view of the superabsorbent fibrous layer 14 as a multi-laminate construction. As illustrated, the fibrous layer 14 is formed as a three part laminate comprising a fluid-permeable, covering stratum 60 having representative pores 62 to indicate the fluid permeable nature of the covering. Underlying this fluid permeable covering stratum 60 is the superabsorbent fibrous material 64 comprising fluid-absorbing fibers able to absorb at least 15 times their own weight of fluid. The preferred form and embodiment of these superabsorbent fibers is as a non-woven absorbent batt composed of a substantially uniform array of superabsorbent fibers 66 (able to absorb not less than 15 times their own weight of fluid) and support fibers 68. While the primary function of the superabsorbent fibers 66 is to absorb high volumes of fluid, the support fibers 68 interlock with the superabsorbent fibers to provide strength and stability for the superabsorbent fibrous batt both before and after it is saturated by fluid. The support fibers 68 also provide good absorbent and adsorbent qualities and offer good resiliency when either in wet or dry states. In general, the superabsorbent fibers 68 typically comprise between 5–50% of the total fiber content for the non-woven absorbent batt 64. Lastly, a fluid-impermeable, supporting material 70 is preferably bonded in a conventionally known manner to the underside of the absorbent batt 64. This fluid-impermeable, supporting material 70 acts to prevent passage and/or transport of fluid previously absorbed in the absorbent batt 64 from passing onto any other surface or material including the planar support sheet 12.

The multi-laminate construction preferred as the superabsorbent fibrous layer 14 may be manufactured and supplied in roll form as shown by FIG. 8. In this construction and manufacture, the fluid-impermeable supporting material 70 (serving primarily as an impermeable bottom sheet for the multi-part construction) may be extended along the sides and edges of the non-woven absorbent batt 64 and be extended to overlay the top edges of the fluid-permeable covering stratum 60— thereby providing peripheral side shields 72 and 74 for the multi-laminate construction as a whole. In keeping with the optional replaceable and disposable formats for the superabsorbent fibrous layer 14 as described previously, FIG. 8 illustrates a roll of the preferred three part constructed, superabsorbent fibrous layer 14—a specific dimensioned segment of which is removed by cutting along the line aa' as indicated. Subsequently, the cut ends of the multi-laminate construction may then also be optionally folded over along its edges as illustrated to provide additional side shields 76 and 78. Accordingly, as seen in FIG. 9, the protective side shields 72, 74, 76, and 78 respectively would provide additional but optional effective barriers against the overflow of fluids or liquids absorbed by the absorbent batt 64 and maintain the overall integrity, strength, and multi-laminate construction of the superabsorbent layer 14.

It will be noted and appreciated that the preferred multi-laminate construction for the superabsorbent layer 14 as described herein is part of the subject matter described and claimed within copending patent application of Conrad A. D'Elia and John D. Hogan entitled "Superabsorbent Non-woven Fibrous Material," the text of which is expressly incorporated by reference herein. In addition, the most preferred composition and blend of fiber materials to be described subsequently also comprises a major part of the above identified, copending patent application. Preferably, the superabsorbent fibers 66 employed in the non-woven absorbent batt 64 within the multi-laminate construction is a fiber formed from a blend of heterocyclic carbonate and a copolymer of maleic anhydride and isobutylene, as described in U.S. Pat. Nos. 4,616,063; 4,705,773; 4,731,067; 4,743,244; 4,788,237; and 4,813,945 respectively—the text of which are also individually incorporated by reference herein for their disclosures.

For optimal absorptive function by the non-woven absorbent batt 64, the superabsorbent fibers 66 are mixed with support fibers 68, preferably using several deniers of polyester. A variety of other materials and compositions may also be used for the support fibers themselves. These include: rayon, cotton, polypropylene, nylon, and polyethylene. These support fibers, regardless of specific composition or materials, should interlock with the superabsorbent fibers, preferrably in a non-woven manner. In addition, although a great range of percentage content for the support fibers may be utilized, the percentage ratio of support fibers typically comprises 50–95% of the total fiber content for the absorbent batt 64.

The fluid absorption characteristics and volume capacity of the superabsorbent fibrous layer 14 (as noted by the disclosure within copending application of Messers. D'Elia and Hogan) are determined by many factors including superabsorbent fiber content, the composition of the support fiber material, batt density and padding size. It is recognized also that the horizontal and vertical water retention properties of the absorbent fibrous layer will vary markedly with alterations in the nature and percentage content of superabsorbent fiber versus support fiber, the denier, the fabric weight, and the composition of the support fiber. If and when the preferred blend of heterocyclic carbonate and copolymer of maleic anhydride and isobutylene is employed, polyester is the most desirable material for use as the support fiber for combination with the superabsorbent fiber. Polyester contributes excellent absorbency properties adjunct and complementary to those of the absorption fibers themselves when present in sufficient density. Moreover, whenever finer denier of support polyester fibers is employed, the overall fluid retention capacity is clearly increased such that various embodiments of the preferred materials are able to absorb 60 fold and sometimes up to 100 fold their product weight of water or other fluid.

To illustrate and to understand how the multi-laminate preferred construction for the superabsorbent fibrous layer works, FIG. 10 illustrates a cross-sectional view of the multi-laminate construct in greater detail. The support fibers 68 are shown as solid lines while the superabsorbent fibers 66 are provided as dashed lines so that they can be distinguished from one another. The fluid-permeable covering stratum 66 permits the migration of fluids such as water and is typically hydrophobic to facilitate complete and rapid migration and transfer of fluid to the absorbent batt 64 beneath it. An added and desirable function of the covering stratum 60 is to provide a smooth sliding surface of low surface tension which presents a relatively small coefficient of friction upon which the skin of the patient, organs, or instruments may be readily moved without tearing the absorbent batt material whether in dry or saturated form. The fluid impermeable supporting material 70 acts as a bottom sheet and is desirably any suitably water-impervious and tear resistant material. This fluid-impermeable material may be folded, corrugated, or embossed to facilitate an increased wicking of fluid through the absorbent batt thereby encouraging effective distribution of absorbed fluid throughout the entirety of the absorbent batt 64. In the unused, dry state, both the superabsorption fibers and the support fibers may criss-cross and bend as indicated within FIG. 10. When the absorbent batt 64 absorbs fluid and becomes wet, the superabsorbent fibers 66 can swell to many times their original dry size, up to and including about 100 times their diameter when dry. In addition, the swelling of the superabsorbent fibers upon wetting exerts force upon the support fibers 68 in the batt and stiffens them. Accordingly, in many instances, the absorbent batt forces fibers which are only loosely crossed and meshed in the dry state to tightly lock and support each other in the wetted fluid absorbent state. This mechanism is believed to account in part at least for the superabsorption capability of the fibrous layer to retain its physical integrity even when holding many times its weight in fluid.

It should be noted and appreciated also that a wide range and diversity of other compounds and chemical compositions are believed to be conventionally available and known as substitutes and replacements for the preferred composition for superabsorbent fibers as described above. The range, variety, and diversity of such superabsorbent fluid materials and compositions is described within the following publications: water absorbing acrylic copolymer compositions prepared from acrylic acid monomers and hydrophilic unsaturated carbonate monomers as described within Japanese Patent Publication No. 63242344(881017); the water absorptive composites of impregnated natural or synthetic fibers with modified acrylic acid described within European Patent Publication No. 290814(881117); water-swellable cross-linked polymers of vinyl-saccharide monomer as described by European Patent Publication No. 283090(880921); a super-absorbent for blood and proteinaceous fluid comprising insoluble ionic macromolecular material in acidic form as described within French Patent No. 2602985(880226); water absorptive fibrous composite materials containing polymerized partially neutralized acrylic acid which is cross-linked using glycidyl ether compounds as described by European Patent Publication No. 262405(880406); an absorbent fibrous material comprising cross-linked polysaccharides as described in European Patent Publication No. 232121(870812); water-absorbing polymer compounds prepared by polymerization of acrylic acid (alkali metal) salts in the presence of alpha-olefins and carboxylic acids as described within Japanese Patent Publication No. 62053310(870309); a fluid absorbing composition comprising water soluble carboxylic polyelectrolyte cross-linked with di- or polyfunctional aziridine as described within U.S. Pat. No. 4,645,789; and the foam forming compositions as described within British Patent No. 2136813. It will be recognized and appreciated that the provided listing is merely illustrative and clearly non-exhaustive in its coverage. Many other fluid absorbing materials able to be manufactured and to provide a superabsorbent capability—that is, able to absorb at least 15 times its own weight in fluid—are clearly available and commercially sold today. All such conventionally known chemical compositions, manufacturers, and superabsorbent materials are deemed to be within the scope of the present invention.

The present invention is not to be limited in scope nor restricted in form except by the claims appended hereto.

What I claim is:

1. A portable superabsorbent stretcher and erectable on-demand isolation tent article comprising:
   at least one planar support sheet having a determinable configuration and dimensions;
   at least one superabsorbent fibrous layer disposed upon said support sheet, said superabsorbent layer comprising fluid-absorbing fibers able to absorb at least fifteen times their own weight of fluid;
   a collapsed isolation tent joined to said support sheet, said collapsed isolation tent being erectable on-demand to envelop and isolate said superabsorbent fibrous layer and the airspace adjacent to said superabsorbent fibrous layer;
   portable erecting means attachable at least in part to said isolation tent for erecting said collapsed isolation tent on-demand; and
   portable transporting means attached at least in part to said support sheet for transporting said support sheet, said superabsorbent fibrous layer, and said isolation tent in collapsed and erected states.

2. A portable and disposable superabsorbent stretcher and erectable in-demand tent article comprising:
   at least one disposable planar support sheet having a determinable configuration and dimensions;
   at least one disposable superabsorbent fibrous layer disposed upon said support sheet, said superabsorbent layer comprising fluid-absorbing fibers able to absorb at least fifteen times their own weight of fluid;

a disposable, collapsed isolation tent joined to said support sheet, said collapsed isolation tent being erectable on-demand to envelop and isolate said superabsorbent fibrous layer and the airspace adjacent to said superabsorbent fibrous layer;

portable and disposable erecting means attachable at least in part to said isolation tent for erecting said collapsed isolation tent on-demand; and portable and disposable transporting means attached at least in part to said support sheet for transporting said support sheet, said superabsorbent fibrous layer, and said isolation tent in collapsed and erected states.

3. A portable superabsorbent stretcher and erected isolation tent article comprising:

at least one planar sheet having a determinable configuration and dimensions;

at least one superabsorbent fibrous layer disposed upon said support sheet, said superabsorbent layer comprising fluid-absorbing fibers able to absorb at least fifteen times their own weight of fluid;

an erected isolation tent joined to said support sheet, said erected isolation tent enveloping and isolating the airspace adjacent to said superabsorbent fibrous layer, said erected isolation tent being collapsible on-demand;

portable maintaining means attachable at least in part to said isolation tent for maintaining said isolation tent in an erected state; and portable transporting means attached at least in part to said support sheet for transporting said support sheet, said superabsorbent fibrous layer, and said isolation tent in collapsed and erected states.

4. The portable stretcher and isolation tent article as recited in claim 1, 2, or 3 wherein said superabsorbent fibrous layer comprises a mixture of support fibers and said fluid-absorbing fibers.

5. The portable stretcher and isolation tent article as recited in claim 4 wherein said support fibers comprise a polyester compound.

6. The portable stretcher and isolation tent article as recited in claim 4 wherein said mixture of fibers comprises a non-woven array of fibers.

7. The portable stretcher and isolation tent article as recited in claim 1, 2, or 3 wherein said fluid-absorbing fibers comprise a heterocyclic carbonate and a copolymer of maleic anhydride and isobutylene.

8. The portable stretcher and isolation tent article as recited in claim 1, 2, or 3 wherein said superabsorbent fibrous layer can absorb up to fifty times its weight of fluid.

9. The portable stretcher and isolation tent article as recited in claim 1, 2, or 3 wherein said superabsorbent fibrous layer further comprises a fluid-permeable covering stratum applied to one surface of said fibrous layer.

10. The portable stretcher and isolation tent article as recited in claim 1, 2, or 3 wherein said superabsorbent fibrous layer further comprises a fluid-impermeable, supporting material applied to one surface of said fibrous layer.

11. The portable stretcher and isolation tent article as recited in claim 1, 2, or 3 wherein said superabsorbent fibrous layer further comprises at least one disinfecting agent.

12. The portable stretcher and isolation tent article as recited in claim 1, 2, or 3 wherein said isolation tent is fabricated of transparent material.

13. The portable stretcher and isolation tent article as recited in claim 1, 2, or 3 wherein said isolation tent comprises a heat-reflecting material.

14. The portable stretcher and isolation tent article as recited in claim 1, 2, or 3 further comprising means located on said tent for accessing the interior of said tent.

15. The portable stretcher and isolation tent article as recited in claim 1, 2, or 3 further comprising portable means able to communicate with the interior of said isolation tent when erected to decontaminate air-borne particles enveloped and isolated by said erected tent.

16. The portable stretcher and isolation tent article as recited in claim 1, 2, or 3 wherein said stretcher and isolation tent has been sterilized in advance of use.

17. The portable stretcher and isolation tent article as recited in claim 1, 2, or 3 wherein said planar support sheet is formed of weight-bearing material.

18. The portable stretcher and isolation tent article as recited in claim 1, 2, or 3 further comprising at least one rigid sheet for additional support.

* * * * *